United States Patent
Osorio et al.

(10) Patent No.: US 6,560,486 B1
(45) Date of Patent: May 6, 2003

(54) BI-DIRECTIONAL CEREBRAL INTERFACE SYSTEM

(76) Inventors: Ivan Osorio, 4005 W. 124th St., Leawood, KS (US) 66209; Mark Frei, 3116 W. 23rd Ter., Lawrence, KS (US) 66047

( * ) Notice: Subject to any disclaimer, the term of this patent is extended or adjusted under 35 U.S.C. 154(b) by 0 days.

(21) Appl. No.: 09/416,471

(22) Filed: Oct. 12, 1999

(51) Int. Cl.[7] .................. A61N 1/375; A61B 5/0476
(52) U.S. Cl. .................. 607/45; 600/544; 600/607; 600/36
(58) Field of Search .................. 600/300, 378, 600/377, 383, 544, 545; 607/2, 45, 62, 36; 340/573.1

(56) References Cited

U.S. PATENT DOCUMENTS

| | | | | |
|---|---|---|---|---|
| 4,127,110 A | * | 11/1978 | Bullara | 128/2 |
| 4,186,749 A | * | 2/1980 | Fryer | 128/748 |
| 4,471,786 A | * | 9/1984 | Inagaki et al. | 128/748 |
| 5,159,927 A | * | 11/1992 | Schmid | 128/419 |
| 5,220,929 A | * | 6/1993 | Marquit | 128/898 |
| 5,480,416 A | * | 1/1996 | Garcia et al. | 607/36 |
| 5,549,620 A | * | 8/1996 | Bremer | 606/151 |
| 5,928,272 A | * | 7/1999 | Adkins et al. | 607/45 |
| 6,113,553 A | * | 9/2000 | Chubbuck | 600/561 |
| 6,134,474 A | * | 10/2000 | Fischell et al. | 607/45 |
| 6,185,455 B1 | * | 2/2001 | Loeb et al. | 607/3 |

\* cited by examiner

*Primary Examiner*—Kennedy Schaetzle
(74) *Attorney, Agent, or Firm*—Donald R. Schoonover

(57) ABSTRACT

A cerebral interface system has a housing mechanism configured to be at least partially spaced in a cavity formed in the subject's skull; an attaching mechanism for attaching the housing mechanism to the subject's skull; a sealing mechanism for providing a fluid-tight seal between the housing mechanism and the subject's skull; a control mechanism spaced within the housing mechanism; a communication mechanism with one or more sensors embedded in the subject's brain connecting the control mechanism to the subject's brain; and a power source spaced within the housing mechanism. Preferably, an inner wall thereof is substantially aligned with the surrounding inner surface of the subject's skull and an outer wall thereof is substantially aligned with the surrounding outer surface of the subject's skull, or may include an auxiliary portion extending tangentially outwardly from the cavity formed in the subject's skull and having substantially the same profile as the subject's skull thereunder. The system may include a communication link wirelessly connecting the control mechanism to external apparatus for transmitting or receiving information related to detecting, predicting, controlling, or aborting abnormal brain activity of the subject. Alternatively, the control mechanism may be self-contained without need for such external apparatus. An output mechanism is provided that is activatable by the control mechanism. The attaching mechanism may include removable fastening means. The housing mechanism is preferably constructed of titanium. The invention also comprises a method for practicing the invention.

60 Claims, 4 Drawing Sheets

BI-DIRECTIONAL CEREBRAL INTERFACE SYSTEM

BACKGROUND OF THE INVENTION

1. Field of the Invention

The present invention relates to the field of neuroscience and, more particularly without limitation, to a subfield of neuroprostheses for housing devices in close proximity to the brain.

2. Glossary of Terms and Useful Definitions

The term "electroencephalogram" ("EEG") refers to voltage potentials recorded from the scalp and encompasses any recordings obtained from a source outside the dura mater. The term "electrocorticogram" ("ECoG") refers to voltage potentials recorded intracranially, e.g., directly from the cortex. "EKG" is an abbreviation for the term "electrocardiogram," "EMG" for the term "electromyogram" which records electrical muscle activity, and "EOG" for the term "electrooculogram" which records eye movements.

The term "real-time" as used herein describes a system with negligible latency between input and output.

As used herein, the term "outer table" refers to the outer bony sheet of the skull in contact with the scalp; the term "inner table" refers to the inner bony sheet of the skull in contact with the outermost brain membrane or "dura"; and the term "diploe" refers to the part of the skull between the outer table and inner table that provides nutrients and minerals necessary for developing and maintaining the skull.

3. Description of the Related Art

Humans and animals have several normal states of behavior, such as wakefulness and sleep, as well as multiple sub-states, such as attentive wakefulness and REM sleep. Abnormal states of behavior in humans and animals include reversible states, such as seizures, and progressive irreversible states, such as dementia.

Recent advances in the field of clinical neurosciences have opened a new era for the use of and need for implantable therapeutic devices. For example, the use of prostheses, for the diagnosis or treatment of neurologic illnesses, is rapidly growing and will continue to expand as new applications are found. As new technological developments take place, so does the opportunity to improve current designs or performance, decrease power requirements or cost, or minimize complications associated with chronic implantation. For instance, a device to electrically stimulate brain regions, via chronically implanted electrodes for Parkinson's disease, has been recently approved for commercial use by the Food and Drug Administration. Implantable devices to detect and control abnormal brain states, such as epileptic seizures, are currently under development (see Osorio et al., *Epilepsia* 39(6):615–627, 1998).

Currently, brain devices, such as the one used for Parkinson's disease, are implanted under the collarbones at a substantial distance from the brain. For example, the use of wires or conductors to carry a signal into or out of the brain, requires a special, time consuming procedure and careful placement of wires and connectors to avoid scalp/skin erosion, a common and serious complication which often requires removal of the device with loss of benefit to the subject. More specifically, such an approach has several significant disadvantages: (i) the long conductors for connecting the device to electrodes implanted in the brain require tunneling under the scalp and skin, thereby requiring prolonged surgical and anesthesia for installation; (ii) the tract along the conductors often becomes infected requiring, in many cases, that the conductors be explanted with consequent cessation of treatment to the subject; (iii) the conductors often erode the overlying scalp, forcing removal of the cables so that healing can take place but, at the same time, removing the means for warning of or treating impending abnormal activities; (iv) the conductors often fracture since they are subjected to torsional and other forces generated by normal head/neck movements with consequent corrective surgery to replace the faulty conductors; and (v) in the case of telemetered signals, closer proximity of the emitter to the receiver would increase fidelity of the transmitted signals and decrease power requirements, hence prolonging battery life and decreasing frequency of surgical replacement procedures.

The placement of prior art brain devices outside the skull, such as in the infraclavicular regions, is due to lack of space between the brain and the skull to position such devices and also to the inability to convert virtual into real spaces without affecting the integrity of the skull. Indeed, while the brain is closely apposed to the inner table of the skull, leaving no usable space to safely house any device, the skull has several properties that enable conversion of virtual into real space for use of the integrated ergonomic placement of devices. These properties, which have not been heretofore exploited, include:

a) sufficient wall thickness to allow housing of access systems/electronic components partially or completely within the confines of the two tables of the skull;

b) high tensile strength; and c) semi-circular configuration allowing equal distribution of forces over its surface.

In addition, scalp tissue has the elasticity or deformability necessary for accommodation of housing devices.

Accurate and reproducible prediction of behavioral or biologic signal changes associated with abnormal brain activities has not been generally possible as such events typically occur unpredictably. This limitation has been recently overcome, making it possible to accurately predict various types of brain states, such as epileptic seizures, etc., as taught in U.S. Pat. No. 5,995,868.

Thus, what is needed is a cerebral interface system that permits spacing essential mechanisms, which perform these or other tasks in close proximity to a subject's brain.

SUMMARY OF THE INVENTION

The present invention includes improvements for enabling simultaneous accessibility between the brain of a subject and the outside world for direct application of measures to monitor and analyze the brain activity of the subject, to predict or detect changes in such brain activity, and to allow warning, recording, preventing, and/or controlling undesirable changes in such brain activity, such as the activity changes associated with an epileptic seizure, for example.

The present inventive cerebral interface system for sensing and/or controlling normal or abnormal brain activity in a subject includes: a brain access mechanism comprising a housing mechanism configured to be spaced in a cavity formed in the subject's skull; an attaching mechanism configured to attach the housing mechanism to the subject's skull; a sealing mechanism configured to provide a fluid-tight seal between the housing mechanism and the subject's skull; a control mechanism or signal processor, such as a properly programmed microprocessor, spaced within the housing mechanism; a communication mechanism, which may include one or more sensors implanted in the subject's brain, configured to communicatingly connect the subject's brain to the control mechanism; and a power source configured to operatively power the apparatus.

Preferably, the housing mechanism includes an inner wall having an inner surface substantially aligned with the inner table of the subject's skull. The inner wall may include one or more ports such that a connector or connectors of the communication mechanism can extend through the port or ports into the subject's brain. For this arrangement, the sealing mechanism may include a fluid-tight seal between the connector or connectors and the inner wall. The sealing mechanism may include a bio-compatible coating, a layer of resilient bio-compatible materials such as silicon, polyurethane, or plastic encircling the housing mechanism, etc.

The housing mechanism, which is preferably oval shaped, may include an outer wall having an outer surface that is substantially aligned with the outer table of the subject's skull. In that event, the housing mechanism may include a flanged edge configured to be spaced in abutting engagement with an outer surface of the outer table of the subject's skull. Alternatively, the housing mechanism may comprise an auxiliary housing portion that extends tangentially outwardly from the cavity formed in the subject's skull. Some of the control mechanism may be spaced within the auxiliary housing portion. Preferably, the auxiliary housing portion has substantially the same profile as the subject's skull thereunder, with the peripheral edges thereof grading into an outer surface of the subject's skull.

The brain access mechanism may include a communication link configured to connect the control mechanism in wireless communication with an apparatus external to the subject. The control mechanism, in conjunction with the communication mechanism and the communication link, may be configured to transmit signals from the subject's brain to the external apparatus, which may be configured to detect and predict abnormal brain activity of the subject. Further, the system may include an output mechanism, with the control mechanism, in conjunction with the communication link, configured to receive output signals from the external apparatus, and, in response to the output signals indicating such detection and/or prediction, activate the output mechanism in response thereto. Alternatively, the control mechanism, in conjunction with the communication mechanism, may be self-contained and configured to operatively detect and predict abnormal brain activity of the subject. In that event, the control mechanism may be configured, upon detecting and predicting abnormal brain activity of the subject, to operatively activate the output mechanism.

The attaching mechanism may include removable fastening means, such as one or more screws advanced into the subject's skull. The housing mechanism, auxiliary housing portion, and preferably removable fastening means are preferably constructed of titanium.

In other words, the present invention involves the transformation of a virtual space of the skull into a real space for the safe ergonomic placement of an access system for interfacing with the brain of a subject. This access system includes a housing for encasing the components necessary for analyzing signals indicative of the subject's brain activity state and for providing means to detect or predict changes in such brain activity state, as well as for providing means to prevent or control such changes in activity state, including treatment of abnormal states. The present invention includes, without limitation improvements in the fields of neurology, neurosurgery, bioengineering, and biocybernetics, which enable real-time analysis of biologic signals, such as those related to an EEG signal and/or an ECoG signal of a subject. Such signals are rapidly, accurately, and automatically analyzed by the present invention in order to, for example:

a) predict or detect and signal the occurrence of an abnormal brain activity, such as an epileptic seizure, in real time or essentially contemporaneously with the arrival of the EEG or ECOG signal at a signal processor;

b) predict behavioral changes typically associated with such abnormal activity;

c) download or telemeter the detection or prediction outputs to devices for warning, therapeutic interventions, and/or the storage of data; and/or d) apply responsive measures to prevent or control such abnormal activity in the brain of a subject.

The bi-directional cerebral interface system, described herein, provides for the safe, ergonomic, cost-effective and energy efficient implantation of a housing device for automated sensing and control of changes in brain states, considerably improving the state of the art.

PRINCIPAL OBJECTS AND ADVANTAGES OF THE INVENTION

The principal objects and advantages of the present invention include: providing a brain access or cerebral interface mechanism mountable in a cavity formed in a subject's skull; providing such a cerebral interface mechanism having a housing mechanism preferably constructed of titanium; providing such a cerebral interface mechanism having an auxiliary housing portion extending tangentially outwardly from such a cavity; providing such a cerebral interface mechanism having a sealing mechanism for providing a fluid-tight seal between a housing mechanism thereof and the subject's skull; providing such a cerebral interface mechanism having a control mechanism, such as a programmed signal processor or microprocessor, spaced therein; providing such a cerebral interface mechanism having a communication mechanism for connecting a control mechanism thereof to the subject's brain; providing such a cerebral interface mechanism having a power source; providing such a cerebral interface mechanism having an inner wall aligned substantially co-planar with the surrounding inner surface of the subject's skull; providing such a cerebral interface mechanism having a communication link for wirelessly connecting a control mechanism thereof to external apparatus; providing such a cerebral interface mechanism having a control mechanism for activating an output mechanism; providing such a cerebral interface mechanism securable to the subject's skull by removable fastening means; and generally providing such a cerebral interface mechanism that is effective in operation, reliable in performance, capable of long operating life, and particularly well adapted for the proposed usages thereof.

Other objects and advantages of the present invention will become apparent from the following description taken in conjunction with the accompanying drawings, which constitute a part of this specification and wherein are set forth exemplary embodiments of the present invention to illustrate various objects and features thereof.

DETAILED DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
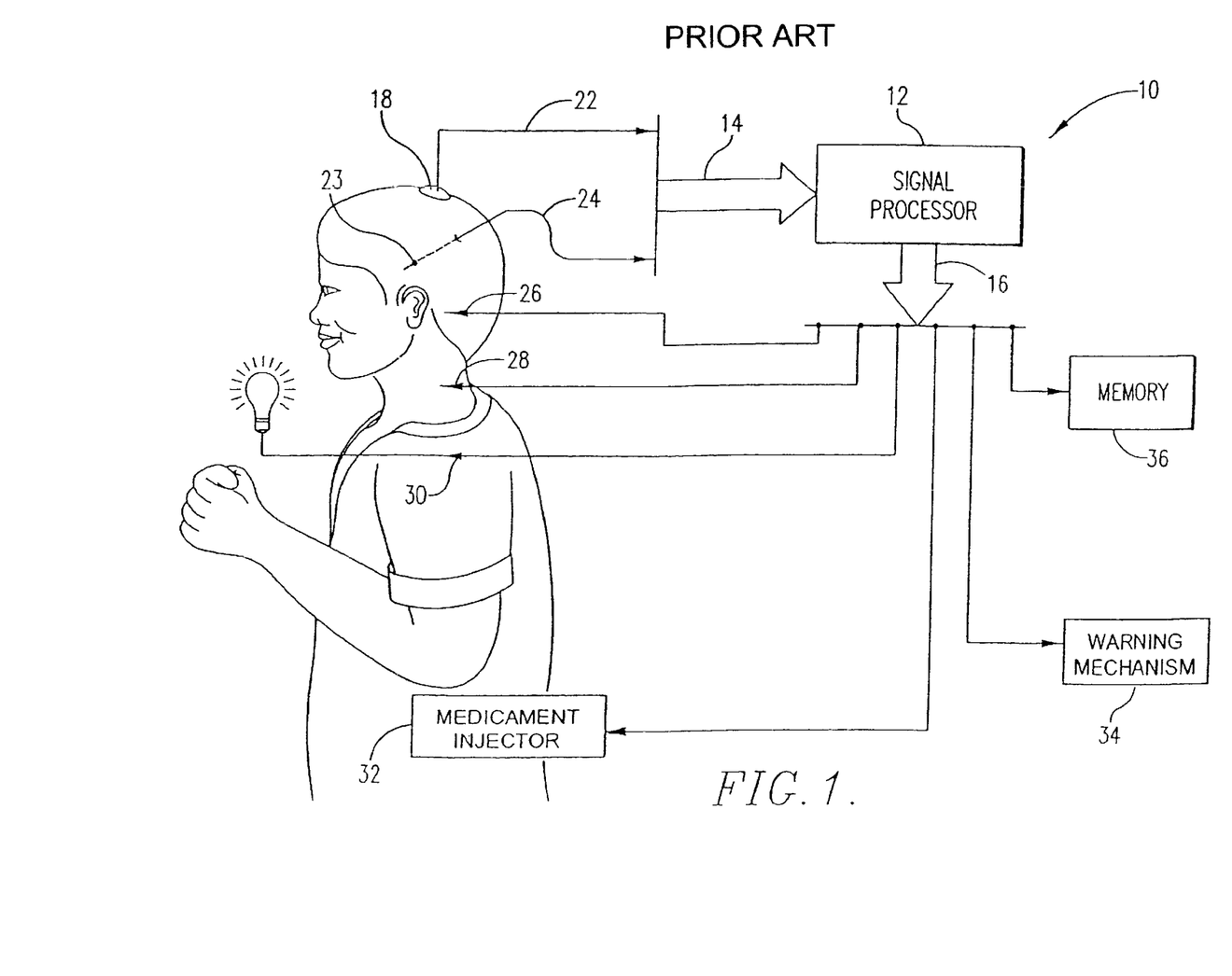
FIG. 1 is a schematic illustration of a prior art system for the prediction, rapid detection, warning, prevention, and control of changes in activity states in the brain of a subject, showing inputs of brain or other biologic system signals of a subject from surface and/or implanted or intracranial sensors to a signal processor and various types of outputs.

A detailed description of a prior art system for the prediction, rapid detection, warning, prevention, and control of changes in activity states in the brain of a subject has been previously disclosed in U.S. Pat. No. 5,995,868, which disclosure is incorporated herein by reference. FIG. 1 thereof, reproduced as FIG. 1 hereof, illustrates an apparatus 10 for receiving and analyzing signals representative of a subject's brain activity and for producing different types of outputs. Apparatus 10 includes signal processor 12, inputs 14 and outputs 16. Signal processor 12 may be a computer, such as one with capabilities that meet or exceed those of an Intel 486-based computer having 33 MHz clockspeed and 8 MB of RAM. Those skilled in the art will appreciate that an appropriate digital signal processor can be used in place of the computer, as could a custom-designed semi-conductor chip having the requisite capability. Signal processor 12 could also be an analog processor or an analog/digital combination.

Inputs 14 include EEG or other type of scalp signals obtained from a plurality of scalp sensors 18 transmitted through associated lines 22, or ECOG signals obtained from implanted sensors 23 and transmitted through associated lines 24. The input signals were amplified and converted from analog to digital form at a rate of 240 Hz with a dynamic range of ±300 mV and digital resolution of 0.59 mV, or ten bits of precision per datum. This arrangement provides 144 Kb of data per minute, per channel. Those skilled in the art will appreciate that sampling may be performed at fixed or varying rates, such as higher or lower than 240 Hz, and precision, with more or less precision than ten bits, using linear or nonlinear analog to digital conversion, and with constant or varying dynamic range, i.e., adjustable gain. Data acquisition may also be performed using adaptive sampling techniques, wherein sampling parameters thereof may vary over time and are determined by characteristics of the signal being sampled. Adaptive sampling techniques can be used to selectively enhance relevant signal characteristics and increase signal quality and resolution in certain frequency bands.

Outputs 16 can be electrodes 26 which may be intracranial or extracranial or placed over or around a nerve 28, a medicament injector or pump 32, an audio or LED output or any other form of warning mechanism 34, and auxiliary memory 36 for storing input signals and event data. Implanted electrodes 26 can be used for any form of activation or deactivation of local or remote brain cells, such as appropriate electrical or thermal applications for example, or for ablation of epileptogenic tissue. Nerve stimulator 28 is preferably associated with the vagus nerve as such stimulation has been found to abate or prevent a seizure; see, e.g., U.S. Pat. Nos. 4,702,254 and 4,867,164 by Zabara. Physiologic or natural stimulation of receptors, such as application of light to retinal receptors for example, can prevent or abate seizures and is a function of stimulator 30. Injector 32 is preferably implanted for automated instantaneous release of an appropriate medicament, inclusive of any efficacious substance, for treating, preventing or abating a seizure. Memory 36 is provided to store signal and event data for archival and analysis purposes.

The analysis performed in the signal processor 12 can be customized for a particular subject to improve both the detection of brain states and state transitions and the prediction of changes in brain states. The customization of the signal processing can be based on the information stored in memory 36 via feedback of such information to signal processor 12. For example, this information may be used to monitor efficacy of treatment and to optimize seizure/spike detection and prediction, and therapeutic or safety interventions. Memory 36 may be included as an integral part of signal processor 12.

Changes in cerebral state are highly correlated with changes in level and type of activity of other organ systems, heart for example, and, as such, these signals from such other organ systems may be useful for detection and prediction or validation of seizures or of other changes in brain state. More specifically, the following signals may be used in conjunction with EEG and ECoG signals for analysis by components housed within the system:

a) non-electrical cerebral global or regional signals, such as concentrations of glucose, free radicals, metabolic by-products, neuro-transmitters, or other substances, or measurements of intracranial pressure, temperature, blood flow or indices of metabolic activity, etc.;

b) cardiovascular signals such as heart rate, R—R interval and variability, etc.;

c) respiratory signals such as tidal volume, peak-to-peak interval, etc.;

d) electrodermal and other DC potentials;

e) signals representative of concentrations in the blood or other peripheral tissues of gases, substances, or chemicals such as lactic acid, etc.;

f) signals representative of the level or type of activity of cranial or peripheral nerves, such as frequency and pattern of action potentials for example;

g) signals related to EMG activity, force, direction, and patterns of limb or body movements; and (h) use of other signals such as EKG, respiratory rate, magnetic fields, thermic potentials, concentrations of chemicals, recordings from a dynamometer or accelerometer attached to the subject or bed, etc.

In many cases it is advantageous to record signals from other sites or organs in addition to the brain or its encasing structures, and to analyze biological signals other than EEG/ECoG, including, but not limited to, (i) other electrical potentials, AC or DC; (ii) EKG; (iii) EMG; (iv) respiratory rate; (v) concentrations of glucose, free radicals, or other substances in the brain such as neurotransmitters for example, blood or other tissues; (vi) magnetic fields; and (vii) brain temperature. It is also important to note that while, for the sake of clarity, attention is primarily focused on data from a single sensor in the example hereinbefore described, the method can be simultaneously applied in parallel to signals from a large number of individual sensors and combinations of sensors, to obtain a weighted sum of the electrical potentials between a given sensor and all other sensors for example, monitoring spatio-temporal correlations of the resulting outputs.

To the extent presently feasible or necessary for a particular application, the cerebral interface system 40 of the present invention includes a brain access or cerebral interface mechanism 41 for interfacing with the brain of the subject, as generally shown in FIGS. 2 through 7. The cerebral interface mechanism 41 includes a housing mechanism 43 configured to be spaced in a cavity 45 formed in a subject's skull 47; attaching means 53 configured to attach the housing mechanism 43 to the subject's skull 47; sealing means 55 configured to provide a fluid-tight seal between the housing mechanism 43 and the subject's skull 47, dura mater, brain 65, and scalp; a control mechanism 57, such as a microprocessor 59, spaced within the housing mechanism 43; a communication mechanism 63 configured to communicatingly connect the subject's brain 65 to the control mechanism 57; and a power source 67 configured to operatively power the brain access mechanism 41, making the cerebral interface system 41 self-contained to the extent feasible or necessary for a particular application.

Figure 2:
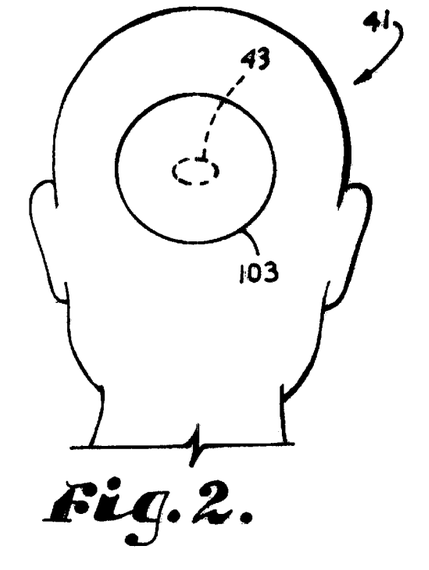
FIG. 2 is a schematic rear view of a subject using a bi-directional cerebral interface system, according to the present invention.
Figure 3:
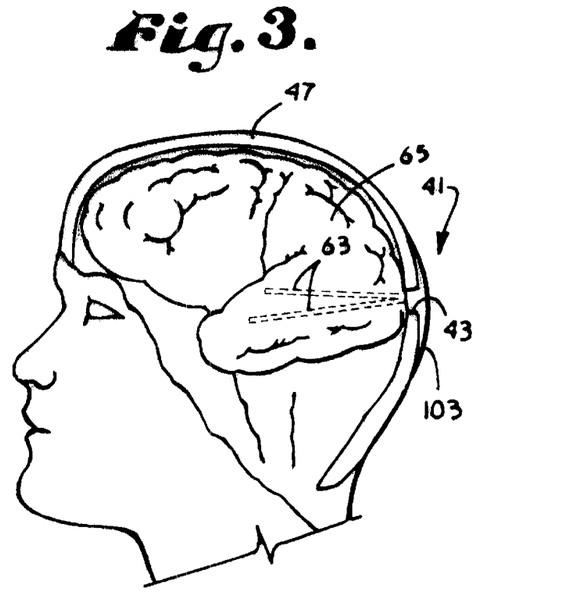
FIG. 3 is a side view of the subject, which portions removed to schematically show connectors of the cerebral interface system inserted into the brain of the subject.

The housing mechanism 43 generally includes an inner wall 73 having an inner surface 75 substantially co-planarly aligned with a surrounding inner surface 77 of the inner table of the subject's skull 47. The primary purpose for such co-planar alignment of the inner surface 75 with the surrounding inner surface 77 is to simulate the original physical surroundings of the subject's brain 65 as closely as possible to avoid unnecessary trauma thereto. If desired for a particular application, dura mater may be removed and the inner wall 73 placed in direct contact with the subject's cerebral spinal fluid. Preferably, the housing mechanism 43 is constructed of titanium or any other suitable, bio-compatible material having necessary physical characteristics. For some applications, it may be desirable for the housing mechanism 43 to be oval shaped, as shown in FIG. 2.

If desired, the inner wall 73 may have one or more ports 83 therethrough. Connectors 85 of the communication mechanism 63 inserted into the subject's brain 65 extend through the port or ports 83, connecting desired locations in the subject's brain 65 to the control mechanism 57. The sealing means 55 is, then, also configured to form a fluid-tight seal between the connectors 85 and the inner wall 73 to prevent leakage of cerebral fluid into the housing mechanism 43. If desired, the sealing means 55 may include a bio-compatible coating, a layer of resilient plastic encircling the housing mechanism 43, or other suitable arrangement. If desired, the communication mechanism 63 may include one or more sensors 86 implanted in the subject's brain 65, such as at the distal end of a connector 85, as shown in FIG. 4.

Figure 4:
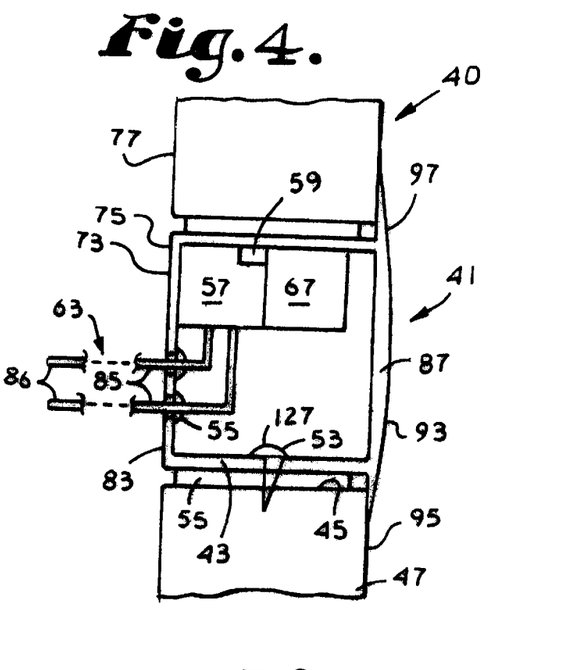
FIG. 4 shows an enlarged and fragmentary, schematic view showing a housing mechanism of the cerebral interface system.

The housing mechanism 43 may also include an outer wall 87 having an outer surface 93 substantially co-planarly aligned with a surrounding outer surface 95 of the subject's skull 47, as shown in FIG. 4. In that event, the housing mechanism 43 preferably has a flanged edge 97 configured to be spaced in abutting engagement with the outer surface 95 of the subject's skull 47.

Figure 5:
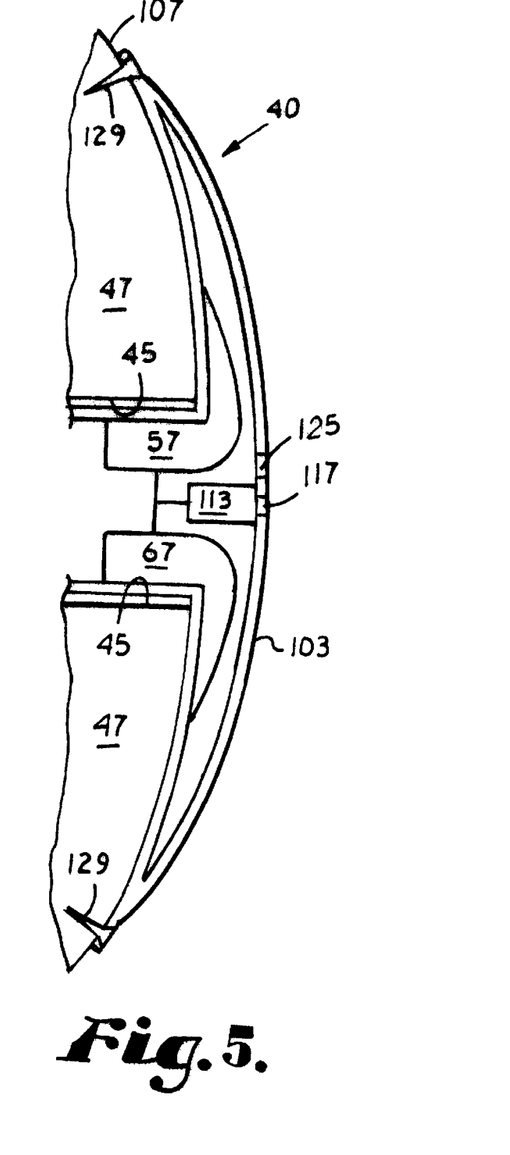
FIG. 5 shows an enlarged and fragmentary, schematic view showing the cerebral interface system having an auxiliary housing portion.

Alternatively and/or additionally, the housing mechanism 43 may further include an auxiliary housing portion 103 that extends tangentially outwardly from the cavity 45 formed in the subject's skull 47. Preferably, the auxiliary housing portion 103 has substantially the same profile as the subject's skull 47 thereunder, with the peripheral edge 105 thereof approximately grading into an outer surface of the subject's skull 107, as shown in FIG. 5. The wafer-like auxiliary housing portion 103 may be hollow such that at least a portion of the control mechanism 57 and/or the power source 67, for example, may be spaced within the auxiliary housing portion 103, as shown in FIG. 5. The auxiliary housing portion 103 is also preferably constructed of titanium or any other suitable, bio-compatible material having necessary physical characteristics.

Figure 7:
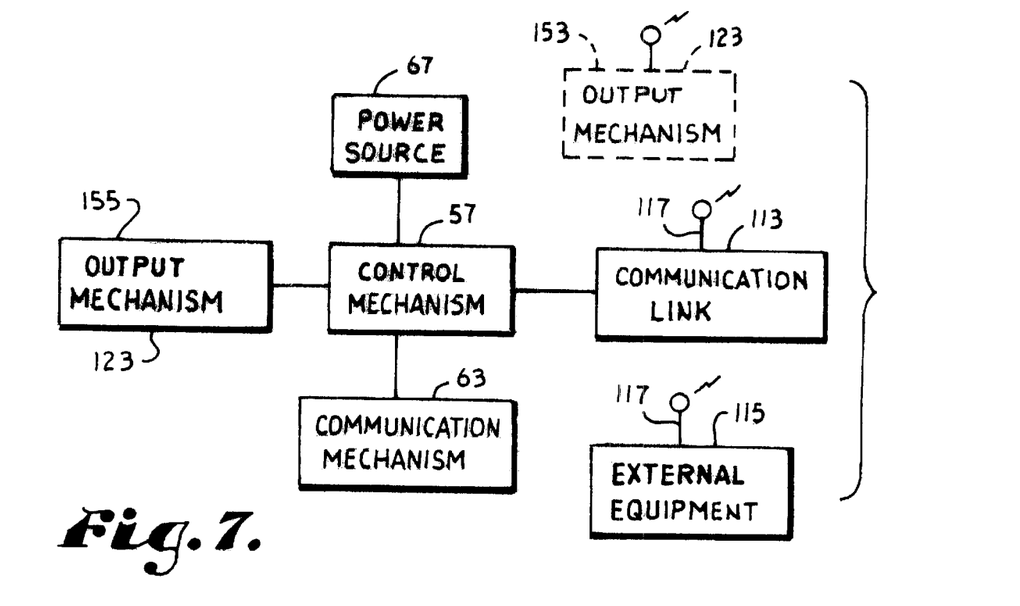
FIG. 7 is a schematic view of the cerebral interface system being used with or without external apparatus and with or without a separate output mechanism.
Figure 8:
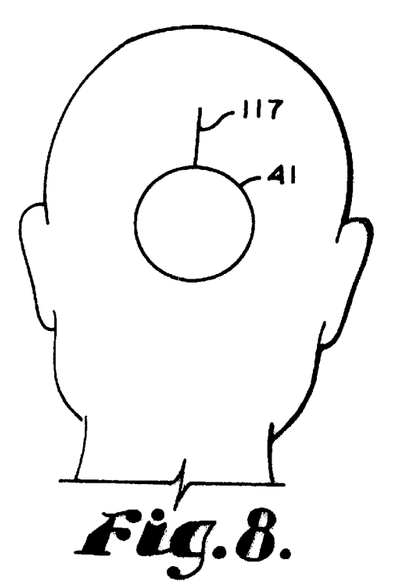
FIG. 8 is a schematic rear view of a subject using the cerebral interface system having an antenna disposed in the scalp of the subject.

The cerebral interface system 40 may also include a communication link 113, as schematically represented shown in FIG. 7, that is configured to connect the control mechanism 57 in wireless communication with apparatus 115 external to the subject, such as through an antenna arrangement 117 known to those skilled in the wireless communication art, as indicated in FIG. 5. In that event, the control mechanism 57, in conjunction with the communication mechanism 63 and the communication link 113, is configured to transmit signals from the subject's brain 65 to the external apparatus 115, wherein the external apparatus 115 is configured to detect and predict abnormal brain activity of the subject. For some applications, it may be desirable to embed the antenna 117 in the scalp of the subject, or in a groove in the skull under the scalp of the subject, as indicated in FIG. 8.

The cerebral interface system 40 may also include an output mechanism 123, as hereinbefore described, and the control mechanism 57, in conjunction with the communication link 113, may be configured to receive output signals from the external apparatus 115 for detecting and/or predicting abnormal brain activity of the subject, and, in response to such output signals indicating such detection and/or prediction, to activate the output mechanism 123 in response thereto. For example, the output mechanism 123 may simply comprise a device, preferably separately powered to conserve the power source 67, to alert the subject, as indicated by the numeral 153 in FIG. 7, or may comprise one or more of the connectors 85 appropriately positioned to thereby apply an electric shock, etc., directly to the subject's brain 65, as indicated by the numeral 155.

Alternatively, the control mechanism 57, in conjunction with the communication mechanism 63, may be configured to operatively detect and predict abnormal brain activity of the subject without the need for external apparatus, such as that designated by the numeral 115. In that event, the control mechanism 57 is configured, upon detecting and predicting abnormal brain activity of the subject, to automatically operatively activate the output mechanism 123. It is to be understood that, even if such self-contained configuration is utilized for a particular application, it may be desirable to selectively access the control mechanism 57, such as through access terminals 125, to ascertain a status of the brain access mechanism 41 and/or the subject.

The attaching means 53 generally includes removable fastening means 127 advanced into the subject's skull 47 that is spaced adjacently to the housing mechanism 43, such as one or more screws for example, as shown in FIG. 4. The attaching means 53 for applications utilizing the auxiliary housing portion 103 of the cerebral interfacing system 40 may include fastening means 129 for attachment to the subject's scull, as shown in FIG. 5.

Figure 6:
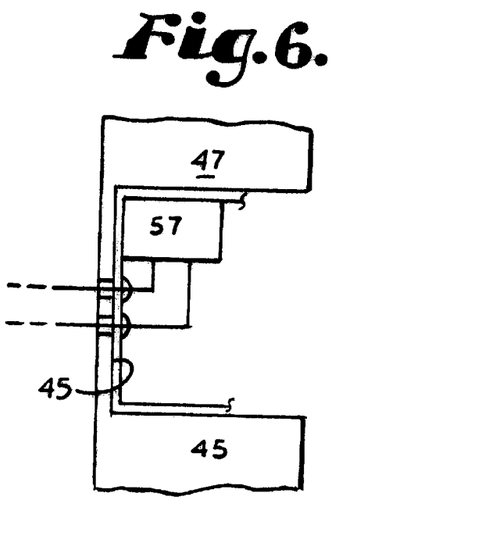
FIG. 6 shows an enlarged and fragmentary, schematic view showing an inner wall of the cerebral interface system implanted in the subject's skull.

The wafer-like auxiliary housing portion 103 serves to both protect the brain and to assist with housing the enclosed electronics of the cerebral interface system 40. The wafer-like brain access mechanism 41 can be manufactured of any material with suitable strength and bio-compatibility to serve as a safe replacement for the removed bone. The width of the housing mechanism 43 may range from being approximately equal to the thickness of the bone of the skull 47 that it replaces to a width as large as that dictated by the inner table, the curvature of the skull, and the elastic properties of the scalp tissues. Depending on the size and complexity of the miniaturized electronics, walls of the housing mechanism 43 may be flat and parallel or may be convex and follow the geodesics or other smooth curves that interpolate the boundary of the skull 47 surrounding the cavity 45 and/or the peripheral edge 105 of the auxiliary housing portion 103. The inner wall 73 may be either implanted within the bone of the skull 47, as shown in FIG. 6, or in direct contact with the dura, as shown in FIG. 4. Preferably, an overall shape of the brain access mechanism 41 can be selected which is not only large enough to house the necessary components, such as miniaturized electronics, telemetry systems, magnetic stimulators, coils, etc., for example, but also be comfortable for the subject.

Figure 9:
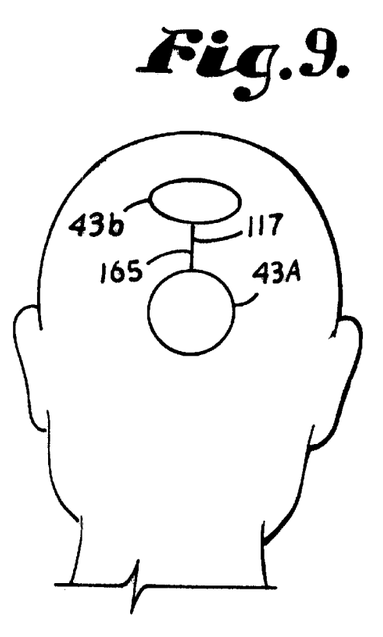
FIG. 9 is a schematic rear view of a subject using the cerebral interface system having two interconnected housing mechanisms of the cerebral interface system, according to the present invention.

It is to be understood that some applications of the cerebral interface system may require that more than one housing mechanism 43 be implanted in the skull of the subject, as indicated by the numerals 43A and 43B in FIG. 9. In that event, it may be desirable to interconnect the contents of the housing mechanisms 43A, 43B by an interconnection 165 comprising one or more conductors. Further, the interconnection 165 may be configured to provide antenna arrangement 117 as necessary for the contents of the housing mechanisms 43A, 43B.

The present invention now makes it possible to safely place devices in the skull by taking advantage of a virtual space, which consists of the actual width or thickness of the skull and the elasticity of the overlying scalp. The width or thickness of the human skull, depending on location, generally ranges between 4–10 millimeters. The virtual space is created by carving out only the diploe and a corresponding portion of the outer table (partial craniotomy), or by removing corresponding portions of both in inner and outer tables of the skull (craniotomy). The diameters of the opening may be as small as necessary but generally not larger than approximately 4×5 centimeters in order to minimize the risk of necrosis of the surrounding bone to which the housing device is attached, such as by screws, glue or other suitable arrangement. The cavity can be located at any desired region of the skull to receive the housing mechanism 43, containing the necessary electronics; more than one device can be placed in a subject's head.

Simply stated, the wafer-like brain access mechanism 41 is intended to house electronic or other devices on and in the skull without impinging or distorting the underlying structures including the brain or altering their protection. The wall or walls of the housing mechanism 43 may be constructed of opaque material. It is to be understood, however, that the wall or walls of the housing mechanism 43 may be constructed of a material or materials that are translucent, transparent, semitransparent, non-attenuating, or partially attenuating for delivery of sound, ultrasound, electromagnetic waves, or other interactive phenomena therethrough directly to the brain of the subject.

It is also to be understood that while certain forms of the present invention have been illustrated and described herein, it is not to be limited to the specific forms or arrangement of parts described and shown.

What is claimed and desired to be secured by Letters Patent is:

1. An apparatus for sensing and controlling changes in brain activity in a subject whether normal or abnormal, comprising:
   (a) a housing mechanism;
   (b) attaching means configured to attach said housing mechanism to the subject's skull;
   (c) a control mechanism spaced within said housing mechanism;
   (d) a communication mechanism configured to communicatingly connect the subject's brain to said control mechanism;
   (e) a power source configured to operatively power said apparatus;
   (f) a communication link configured to connect said control mechanism in wireless communication with a receiving mechanism external to the subject;
   (g) an output mechanism; and
   (h) said control mechanism, in conjunction with said communication link, configured to:
      (1) receive output signals from external equipment configured to detect and/or predict abnormal brain activity of the subject, and
      (2) in response to said output signals indicating such detection and/or prediction, activate said output mechanism in response thereto.

2. The apparatus as set forth in claim 1, wherein said housing mechanism is configured to be flush-mounted relative to the subject's skull.

3. The apparatus as set forth in claim 1, further comprising a warning mechanism spaced within said housing mechanism wherein said warning mechanism is configured to be activated by said control mechanism.

4. The apparatus as set forth in claim 1, further comprising sealing means configured to provide a fluid-tight seal between said housing mechanism and the subject's skull.

5. The apparatus as set forth in claim 4 wherein said sealing means is configured to provide a bio-compatible interface between said housing mechanism and the subject.

6. The apparatus as set forth in claim 5, wherein said interface includes a bio-compatible coating.

7. The apparatus as set forth in claim 5, wherein said interface includes a layer of resilient material.

8. The apparatus as set forth in claim 7, wherein said layer is constructed of plastic.

9. The apparatus as set forth in claim 1, wherein said power source is spaced within said housing mechanism.

10. The apparatus as set forth in claim 1, wherein said housing mechanism is constructed of material that is translucent, transparent, semi-transparent, non-attenuating, or partially attenuating to sound, ultrasound, electromagnetic waves, or other interactive phenomena being applied therethrough directly to the brain of the subject.

11. The apparatus as set forth in claim 1, wherein said housing mechanism includes an inner wall having an inner surface substantially aligned with an inner surface of the subject's skull.

12. The apparatus as set forth in claim 11, wherein:
(a) said inner wall includes at least one port therethrough;
(b) said communication mechanism includes at least one connector extending through said at least one port; and further including
(c) sealing means providing a fluid-tight seal between said at least one connector and said inner wall.

13. The apparatus as set forth in claim 1, wherein said housing mechanism further includes an outer wall having an outer surface substantially aligned with an outer surface of the subject's skull.

14. The apparatus as set forth in claim 1, wherein said housing mechanism is constructed of titanium.

15. The apparatus as set forth in claim 1, wherein said attaching means includes removable fastening means advanced into the subject's skull that is spaced adjacently to said housing mechanism.

16. The apparatus as set forth in claim 15, wherein said removable fastening means includes at least one screw.

17. The apparatus as set forth in claim 1, wherein said housing mechanism includes a flanged edge configured to be spaced in abutting engagement with an outer surface of the subject's skull.

18. The apparatus as set forth in claim 1, wherein said housing mechanism is oval shaped.

19. The apparatus as set forth in claim 1, wherein said control mechanism, in conjunction with said communication mechanism, is configured to operatively detect, predict, warn of, or control changes in a normal or abnormal brain activity state of the subject.

20. The apparatus as set forth in claim 19, further comprising:
(a) an output mechanism; and
(b) said control mechanism being further configured, upon detecting and predicting abnormal brain activity of the subject, to operatively activate said output mechanism.

21. The apparatus as set forth in claim 1, wherein said communication mechanism includes at least one sensor implanted in the subject's brain.

22. The apparatus as set forth in claim 1, wherein said housing mechanism is configured to be spaced in a cavity formed in the subject's skull.

23. The apparatus as set forth in claim 22, wherein said housing mechanism further comprises an auxiliary housing portion extending tangentially outwardly from the cavity formed in the subject's skull.

24. The apparatus as set forth in claim 23, wherein at least a portion of said control mechanism is spaced within said auxiliary housing portion.

25. The apparatus as set forth in claim 23, wherein said attaching means is configured to attach said auxiliary housing portion to the subject's skull.

26. The apparatus as set forth in claim 25, wherein said attaching means includes removable fastening means.

27. The apparatus as set forth in claim 26, wherein said removable fastening means includes at least one screw.

28. The apparatus as set forth in claim 23, wherein said auxiliary housing portion is constructed of titanium.

29. The apparatus as set forth in claim 23, wherein said auxiliary housing portion has substantially the same profile as the subject's skull thereunder, with the edges thereof grading into the outer surface of the subject's skull.

30. The apparatus as set forth in claim 1, wherein said control mechanism includes a microprocessor.

31. An apparatus for sensing and controlling changes in brain activity in a subject whether normal or abnormal, comprising:
(a) a housing mechanism;
(b) attaching means configured to attach said housing mechanism to the subject's skull;
(c) a control mechanism spaced within said housing mechanism;
(d) a communication mechanism configured to communicatingly connect the subject's brain to said control mechanism; and
(e) a power source configured to operatively power said apparatus;
wherein said housing mechanism is configured to be spaced in a cavity formed in the subject's skull and wherein said housing mechanism comprises an auxiliary housing portion extending tangentially outwardly from the cavity formed in the subject's skull.

32. The apparatus as set forth in claim 31, further comprising a communication link configured to connect said control mechanism in wireless communication with a receiving mechanism external to the subject.

33. The apparatus as set forth in claim 32, wherein said control mechanism, in conjunction with said communication mechanism and said communication link, is configured to transmit signals received from the subject's brain to external equipment configured to detect and predict abnormal brain activity of the subject.

34. The apparatus as set forth in claim 32, further comprising:
(a) an output mechanism; and
(b) said control mechanism, in conjunction with said communication link, configured to:
(1) receive output signals from external equipment configured to detect and/or predict abnormal brain activity of the subject, and
(2) in response to said output signals indicating such detection and/or prediction, activate said output mechanism in response thereto.

35. The apparatus as set forth in claim 31, wherein at least a portion of said control mechanism is spaced within said auxiliary housing portion.

36. The apparatus as set forth in claim 31, wherein said attaching means is configured to attach said auxiliary housing portion to the subject's skull.

37. The apparatus as set forth in claim 36, wherein said attaching means includes removable fastening means.

38. The apparatus as set forth in claim 37, wherein said removable fastening means includes at least one screw.

39. The apparatus as set forth in claim 31, wherein said auxiliary housing portion is constructed of titanium.

40. The apparatus as set forth in claim 31, wherein said housing mechanism is constructed of material that is translucent, transparent, semi-transparent, non-attenuating, or partially attenuating to sound, ultrasound, electromagnetic waves, or other interactive phenomena being applied therethrough directly to the brain of the subject.

41. The apparatus as set forth in claim 31, wherein said auxiliary housing portion has substantially the same profile as the subject'skull thereunder, with the edges thereof grading into the outer surface of the subject's skull.

42. The apparatus as set forth in claim 31, further comprising a warning mechanism spaced within said housing mechanism wherein said warning mechanism is configured to be activated by said control mechanism.

43. The apparatus as set forth in claim 31, further comprising sealing means configured to provide a fluid-tight seal between said housing mechanism and the subject's skull.

44. The apparatus as set forth in claim 43 wherein said sealing means is configured to provide a bio-compatible interface between said housing mechanism and the subject.

45. The apparatus as set forth in claim 44, wherein said interface includes a bio-compatible coating.

46. The apparatus as set forth in claim 44, wherein said interface includes a layer of resilient material.

47. The apparatus as set forth in claim 46, wherein said layer is constructed of plastic.

48. The apparatus as set forth in claim 31, wherein said power source is spaced within said housing mechanism.

49. The apparatus as set forth in claim 31, wherein said housing mechanism includes an inner wall having an inner surface substantially aligned with an inner surface of the subject's skull.

50. The apparatus as set forth in claim 49, wherein:
   (a) said inner wall includes at least one port therethrough;
   (b) said communication mechanism includes at least one connector extending through said at least one port; and further including
   (c) sealing means providing a fluid-tight seal between said at least one connector and said inner wall.

51. The apparatus as set forth in claim 31, wherein said housing mechanism is constructed of titanium.

52. The apparatus as set forth in claim 31, wherein said attaching means includes removable fastening means advanced into the subject's skull that is spaced adjacently to said housing mechanism.

53. The apparatus as set forth in claim 52, wherein said removable fastening means includes at least one screw.

54. The apparatus as set forth in claim 31, wherein said housing mechanism is oval shaped.

55. The apparatus as set forth in claim 31, wherein said communication mechanism includes at least one sensor implanted in the subject's brain.

56. The apparatus as set forth in claim 31, wherein said attaching means includes removable fastening means.

57. The apparatus as set forth in claim 56, wherein said removable fastening means includes at least one screw.

58. The apparatus as set forth in claim 31, wherein said control mechanism includes a microprocessor.

59. The apparatus as set forth in claim 31, wherein said control mechanism, in conjunction with said communication mechanism, is configured to operatively detect, predict, warn of, or control changes in a normal or abnormal brain activity state of the subject.

60. The apparatus as set forth in claim 31, wherein said housing mechanism includes a flanged edge configured to be spaced in abutting engagement with an outer surface of the subject's skull.

* * * * *